(12) United States Patent
Kitabjian

(10) Patent No.: US 6,450,999 B1
(45) Date of Patent: Sep. 17, 2002

(54) BODY-CONFORMING ABSORBENT ARTICLE

(75) Inventor: Mary S. Kitabjian, North Wales, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 901 days.

(21) Appl. No.: 08/710,907

(22) Filed: Sep. 24, 1996

Related U.S. Application Data

(63) Continuation of application No. 08/314,985, filed on Sep. 29, 1994, now abandoned.

(51) Int. Cl.$^7$ .......................... A61F 13/15; A61F 13/20
(52) U.S. Cl. .................. 604/385.04; 604/387
(58) Field of Search ..................... 604/385.1, 385.2, 604/386, 387, 389–391, 369, 385.01, 385.04

(56) References Cited

U.S. PATENT DOCUMENTS

| | | | |
|---|---|---|---|
| 4,834,739 A | * | 5/1989 | Linker, III et al. |
| 4,917,701 A | * | 3/1990 | Mauinkurve ................ 604/387 |
| 5,098,422 A | * | 3/1992 | Davis et al. ................ 604/390 |
| 5,125,918 A | * | 6/1992 | Seidy ....................... 604/385.1 |

FOREIGN PATENT DOCUMENTS

| | | | | |
|---|---|---|---|---|
| EP | 0337438 | * | 10/1989 | ................ 601/387 |

* cited by examiner

Primary Examiner—John G. Weiss
Assistant Examiner—K. M. Reichle

(57) ABSTRACT

An absorbent product useful for wearing in the crotch portion of an undergarment is disclosed. The absorbent product has an absorbent structure disposed between a body-facing surface and a garment-facing surface, a positioning element operatively connected to the garment-facing surface, and a conforming element. The conforming element include an association of conformable segments which are moveable with respect to one another. The absorbent product is capable of acquiring and maintaining a form which conforms to a user's body surface contours.

8 Claims, 4 Drawing Sheets

BODY-CONFORMING ABSORBENT ARTICLE

This is a continuation of application Ser. No. 08/314,985, filed Sep. 29, 1994 now abandoned.

FIELD OF THE INVENTION

The present invention relates to absorbent products which are worn in the crotch portion of a user's undergarment which have conforming means to allow the absorbent product to be deformed to intimately contact a user's body. Such products are useful as sanitary napkins, panty liners, adult incontinence pads, and the like.

BACKGROUND OF THE INVENTION

Absorbent products such as sanitary napkins, panty liners, adult incontinence pads, and the like, are designed to be worn between a user's body and a relatively close fitting garment such as an undergarment. Such absorbent products are often secured within the undergarment by means of adhesives, generally pressure sensitive adhesives. Recent attempts to avoid adhesives have employed bendable elements, such as metal plates, bars, and the like. These bendable elements are typically single pieces of metal which are generally more rigid than the absorbent body with which they are associated.

Examples of such products include U.S. Pat. No. 5,098,422, which discloses semi-rigid clip means to wrap around an undergarment; EP 446 818, which discloses a hinged clasp comprising two relatively stiff portions to permit bending of one portion with respect to the other portion; EP 467 184, which discloses the use of bendable elements which may be deformed by the user and which will retain its shape during use; and U.S. Pat. Nos. 4,886,513 and 4,865,597, which disclose a flexibly stiff, springy, reinforcing member that will maintain the shape of an absorbent pad, even after deformation.

These references attempt to provide a predetermined form to the absorbent product and/or to tenaciously grasp a user's garment. The products disclosed generally display significant resistance to additional movement once formed to a desired configuration before use.

Relatively rigid bendable plates or bars are used in these products. The user is likely to be aware of the rigidity of the absorbent products during use, and the preformed nature of the products will reduce the ability of the product to closely conform to the user's body. These references do not teach increased conformity with body surfaces.

Therefore, what is needed is an absorbent product having superior conformability to a user's body. Superior conformability increases leakage protection, reduces the need for tenacious positioning means to anchor the product in place during use, and increases the comfort for the user.

SUMMARY OF THE INVENTION

The body-conforming absorbent products of this invention are useful for wearing in the crotch portion of a user's undergarment. The product has an absorbent structure disposed between a body-facing surface and a garment-facing surface. The product also has conforming means including an association of conformable segments. The conforming means allows the absorbent product to acquire and maintain a form corresponding to a user's body surface contours by the action of forces normally exerted upon the absorbent product during use. The garment-facing surface may also have positioning means in order to reduce the movement of the absorbent product within the crotch portion.

Preferably, the conformable means has a Thwing-Albert bending strength of about 1 to about 250 g. At least some of the conforming segments may be disposed transverse to a length dimension of the absorbent product, and in a particularly preferred embodiment, the transverse conforming segments extend in to a tab portion of the product which can be wrapped around at least a portion of the crotch portion of the undergarment.

Additionally, the positioning means associated with the garment-facing surface is preferably a high-friction surface, such as a polymeric foam. The high-friction surface reduces the movement of the product within the undergarment during use.

DETAILED DESCRIPTION OF THE INVENTION

Figure 1:
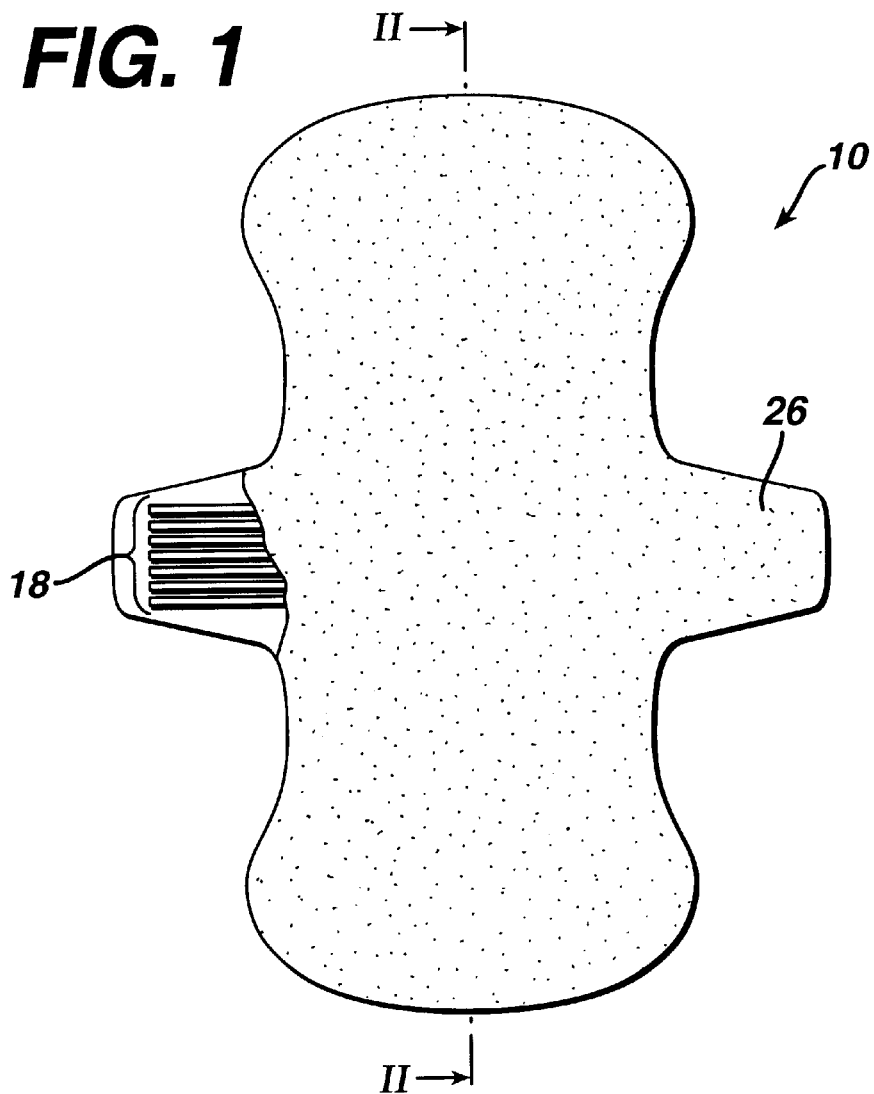
FIG. 1 illustrates a partially broken-away plan view of one embodiment of the present invention having an association of conformable segments spanning the absorbent product in a transverse direction and extending into sidewardly extending tabs.
Figure 2:
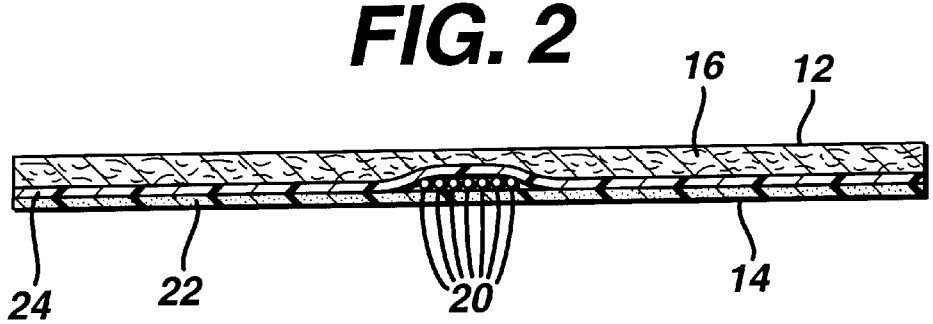
FIG. 2 is a cross-sectional view along line II—II of FIG. 1.

Referring to FIGS. 1 and 2, there is disclosed an absorbent product 10 for wearing in a crotch portion of an undergarment (not shown). The absorbent product 10 has a body-facing surface 12 and a garment-facing surface 14. An absorbent structure 16 is disposed between the body-facing surface 12 and garment-facing surface 14. The absorbent product 10 also has conforming means 18 comprising an association of conformable segments 20. Positioning means 22 are preferably operatively connected to the garment-facing surface 14 of the absorbent product 10. Indeed, the positioning means 22 may define all or a portion of the garment-facing surface 14 of the product 10. Finally, there is a barrier layer 24 disposed below the absorbent structure 16 to prevent absorbed fluids from penetrating completely through the product 10.

The body-facing surface 12 may be a separate component such as a cover sheet, or it may be the exposed surface of the absorbent structure 16 of the product 10. Materials useful as cover sheets include, without limitation, knitted, woven, and nonwoven fabrics, apertured films and fabrics, and the like. The cover sheet may be affixed to the exposed surface of the absorbent structure 16, or it may simply cover and enclose the absorbent structure 16. If the cover sheet is affixed to the exposed surface of the absorbent structure 16, it may be occasionally or completely attached to that surface. This attachment may be formed by embossing, adhesives, heat sealing and the like. If the cover sheet merely encloses the absorbent structure 16, they may be attached to the absorbent structure 16 only at its peripheral edges, or they may not be attached to the absorbent structure 16 at all. For example, the cover sheet may fully enclose the absorbent structure 16 and may be affixed only to the barrier layer 24.

The liquid-impermeable, barrier layer 24 of the product 10 may be, without limitation, a plastic film, an impregnated fabric, flexible, polymeric foam shell and the like. The barrier 24 is preferably formed of a flexible material which is capable of conforming to the user's body surface contours.

The absorbent structure 16 can be any absorbent structure normally used in sanitary protection, feminine hygiene, infant diaper or adult incontinence products. Preferably, the absorbent structure 16 is be formed from materials such as synthetic fibers, including spunbonded, melt blown, card and bind staple fibers; and cellulosic fibers such as wood pulp, stabilized wood pulp, wood pulp with superabsorbent, peat moss board, tissue paper, creped wadding; and the like.

The conforming means 18 include an association of at least two conformable segments 20. Preferably, each conformable segment 20 has a length dimension at least one order of magnitude greater than its diameter or major cross-sectional dimension, more preferably, the length dimension is at least two orders of magnitude greater than the diameter. Each conformable segment 20 may have a generally rectangular or oval cross-section, preferably the cross-section is circular to provide the greatest freedom of bending and lowest cost. Examples of such segments include, without limitation, filaments, wires, strands, fibers, rods, etc.

Preferably, each conformable segment 20 is malleable, i.e., the segment may be deformed or molded to acquire various shapes without breaking. Preferred conformable segments 20 may be formed from metals such as aluminum, copper, brass, bronze, zinc, tin, nickel, and steel; polymers; composites; and the like.

Conformable segments 20 are preferably both stiff and malleable enough to acquire and maintain a shape which conforms to the body surface with which they are associated by action of forces normally exerted on the absorbent product 10 during use. Thus, a conforming means 18 which is too stiff will not acquire a body-conforming shape, while conforming means 18 which are too soft or malleable will not maintain the body-conforming shape once it is acquired. A measure of bending force can help to identify conforming means 18 which may be useful in this invention. A useful measure, TAPPI Routine Control Method RC284, using the Thwing-Albert Score Bend Tester, manufactured by the Thwing-Albert Instrument Company of Philadelphia, Pa., in place of the Ohio Boxboard Scorebend Tester. Preferably, the conforming means 18 has a bending force of about 1 to 250 g, more preferably, about 10 to 150 g, and most preferably, about 15 to 50 g. The conforming means ate tested with a length of 1 inch. The diameter of the wire, or the major axis of oval cross-sectioned segments is preferably between about 0.001 and 0.2 inches, and more preferably about 0.005 to 0.05 inches. Of course, various diameters may be used in conjunction to form the association of conformable segments 20.

The conforming means 18 is made up of an association of conformable segments 20. As used herein the specification and the claims, the term "association" is intended to mean that the conformable segments 20 operate cooperatively, yet separately. Thus, adjacent segments 20 are able to move with respect to one another, while their mechanical characteristics are cumulative as a result of the proximity of adjacent conformable segments 20. The conformable segments 20 may be individual members or they may be segments of a single conformable member which are connected to adjacent segments at their segment ends, such as a single wire folded back and forth across the width or along the length of the absorbent product.

There may be any number of conformable segments, e.g., from 2 to 100 or more. Preferably, there are about 3 to 50 segments, and more preferably, there are about 7 to 30 segments which comprise the conforming means 18. The conforming means 18 may span the entire area of the absorbent product 10, preferably about 5 to 90% of the length of the product 10, and more preferably about 10 to 50% of the length of the product 10. In addition, the conforming means 18 may span the width of the product 10, although preferably, the conforming means 18 spans about 50 to less than about 100% of the width of the absorbent product 10. If the conforming means 18 spans less than the entire length and width of the product 10, it is preferred to leave a region along the peripheral edge of the product 10 which is free of the conforming means 18. This reduces the likelihood that a segment 20 of the conforming means 18 would poke out of the absorbent product 10 and potentially irritate or injure the user.

In the embodiments illustrated in FIGS. 1–4, the conforming means 18 comprises 7 to 9 laterally extending conformable segments 20 of 28 gauge soft aluminum utility wire attached with Dermiform knitted tape (not shown). These wires are arranged in an area of about 2.5 cm by 11.5 cm, are centered on the barrier layer of a SURE & NATURAL PRIMA LIGHT sanitary napkin, and are covered with the tape. This leaves a peripheral margin of at least about 0.1 cm, preferably at least about 0.2 cm, at the side edges of the tabs. In a particularly preferred embodiment, the margin is about 1 cm. Then a layer of polymeric foam 22 is applied to the entire garment-facing side of the product 10.

Figure 7:
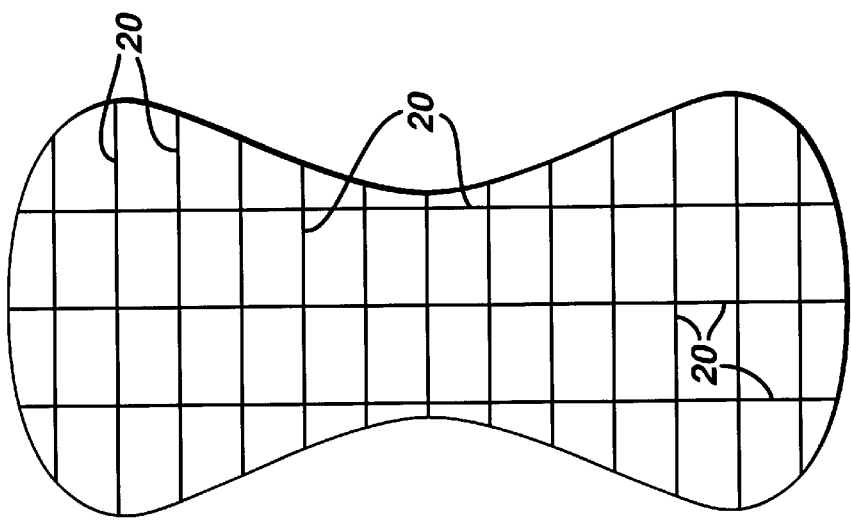
FIGS. 5–7 illustrate alternative patterns of conformable segments in absorbent products according to the present invention.
Figure 6:
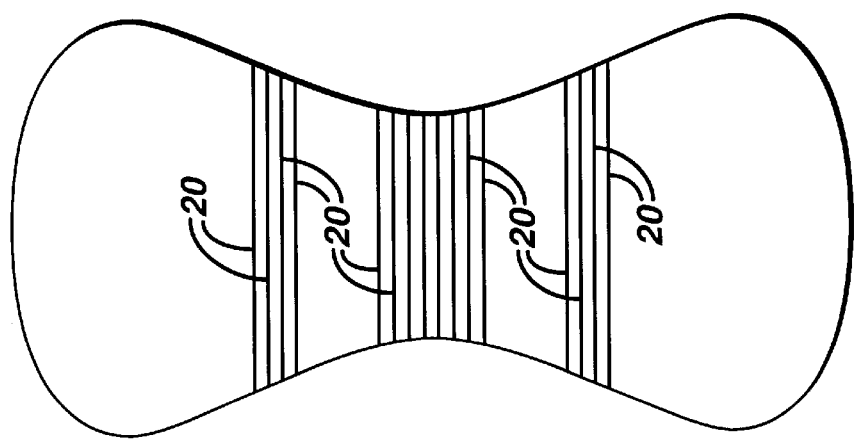
Figure 5:
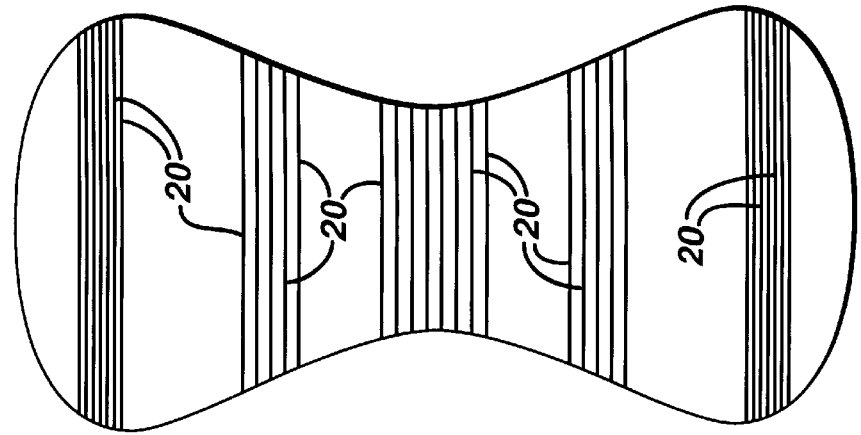

While the invention has been described with reference to the embodiment of FIGS. 1 and 2 above, additional embodiments are contemplated. For example, the conformable segments 20 may be arranged in several transverse groupings as illustrated in FIGS. 5 and 6. At least some conformable segments 20 may also be oriented in a longitudinal orientation as illustrated in FIG. 7. The absorbent product 10 may have any shape useful for employment in the crotch area of a user's undergarment. It may be substantially rectangular, hourglass-shaped with inwardly arcuate side edges, dogbone-shaped with substantially parallel side edges at the center region and a greater width at the longitudinal ends, or other shape normally used in the sanitary protection and adult incontinence field. The absorbent product 10 may also have lateral extensions 26 in the crotch portion for wrapping around a user's undergarment. These extensions may be in the form of "wings" extending along a majority of the side edges or "tabs" which are substantially confined to the center of the crotch portion of the product 10 (See tabs 26 in FIGS. 1 and 3). Of course, the extensions may be of any form, spanning the design options from wings to tabs and modifications in between.

The conforming means 18 is preferably constrained within the absorbent product 10 to prevent conformable segments 20 protruding from the product 10. The conforming means 18 may be constrained by adhesives, lamination, pressure, plastic sheathing, molding, and the like. It is preferred that the chosen constraint permits some relative movement between conformable segments 20 and the rest of the absorbent product 10. The allowed movement reduces the stiffness of the product. For instance, some amount of shear between the conformable segments 20 and the rest of the product 10 allows tabs to be wrapped around a user's undergarment without creating wrinkles as the conformable segments 20 and barrier film 24 will bend through slightly different radii of curvature. The allowed movement also allows the conforming segments 20 to move relative to one another. Conformable segments 20 which touch and/or cross each other can also slide or move relative one to another.

The conformable segments 20 can bend and move essentially independently. They can easily flex and be shaped in any direction. In contrast, both a homogeneous malleable bar and a grid of solidly connected members forming conforming means 18 would be constrained by their geometry.

Figure 8:
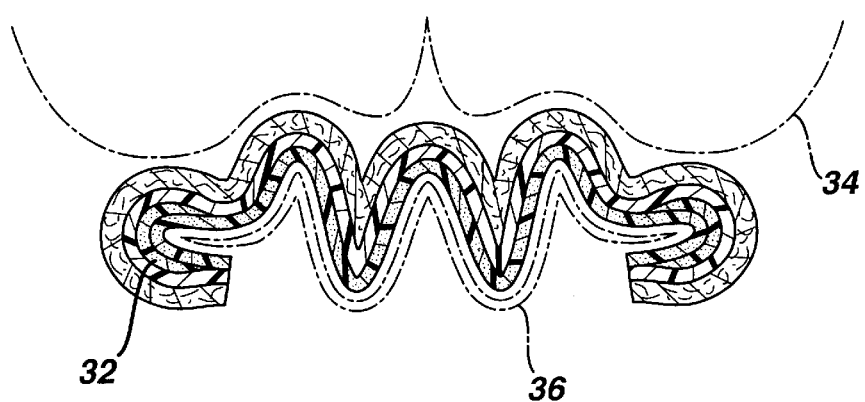
FIG. 8 is a transverse cross-sectional view along line VIII—VIII of the absorbent product of FIG. 3 during use.

Absorbent product 10 of FIGS. 1–2 or 3–4 can be worn by wrapping the tabs 26 around a user's undergarment. During use, deformation forces exerted by the user's body, e.g., thighs, buttocks, crotch, pubis, labia, etc., can conform the product 10 to the user's body surface contours. A lateral cross-section along line VIII—VIII in FIG. 3 after use takes on a "W" shape as illustrated in FIG. 8. The absorbent product 10 is able to assume an interlocking shape with the user's labia. In contrast, a similar product having a single homogeneous bar forming the conforming means 18 resulted in an inverted "U" shape in lateral cross-section after use.

Figure 3:
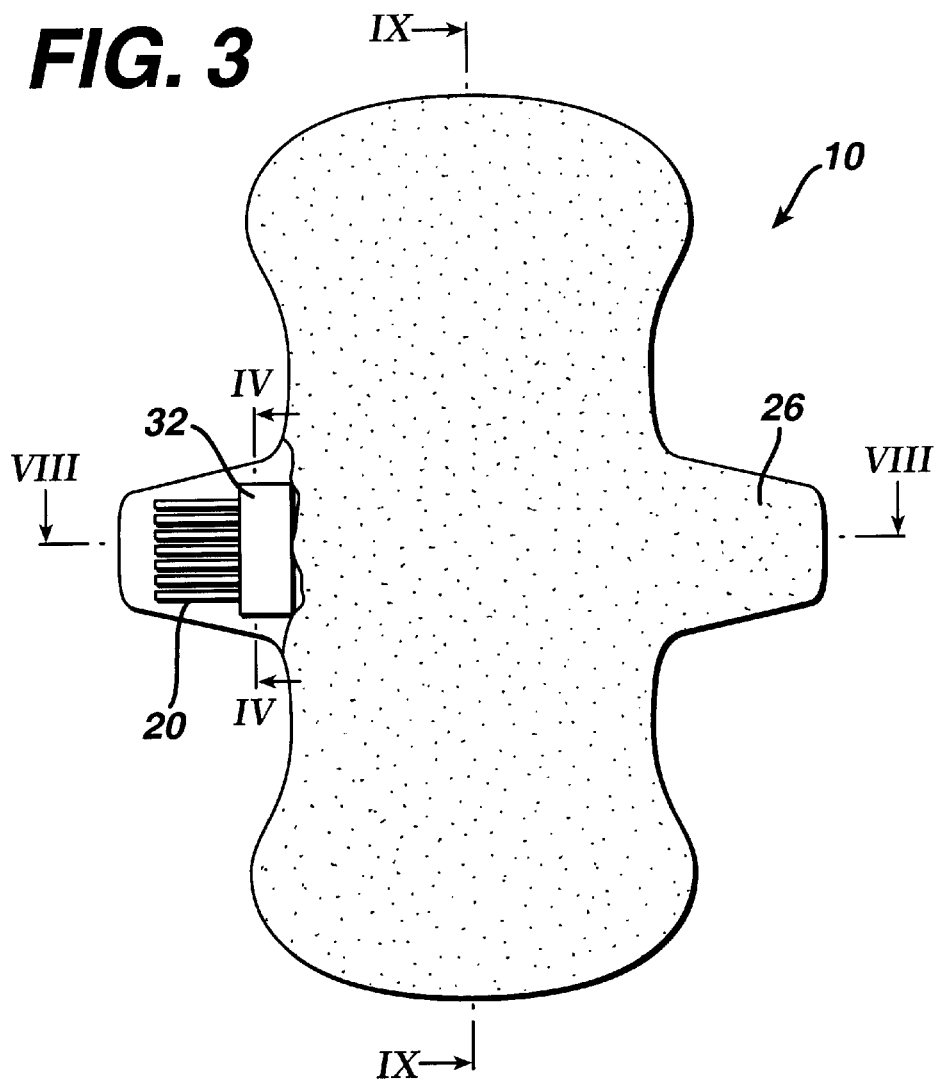
FIG. 3 illustrates a partially broken-away plan view of another embodiment of the present invention having an association of conformable segments spanning the absorbent product in a transverse direction, extending into sidewardly extending tabs, and protected by cushioning means in regions where the conforming means is likely to be severely bent.
Figure 4:
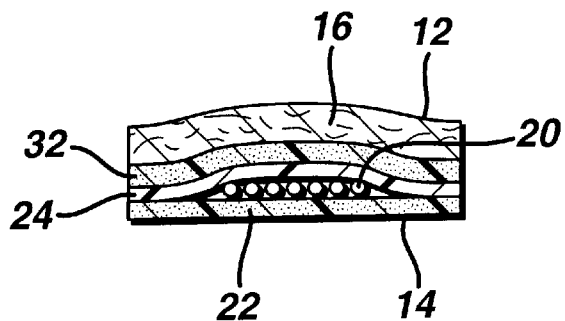
FIG. 4 is a cross-sectional view along line IV—IV of FIG. 3.
Figure 9:
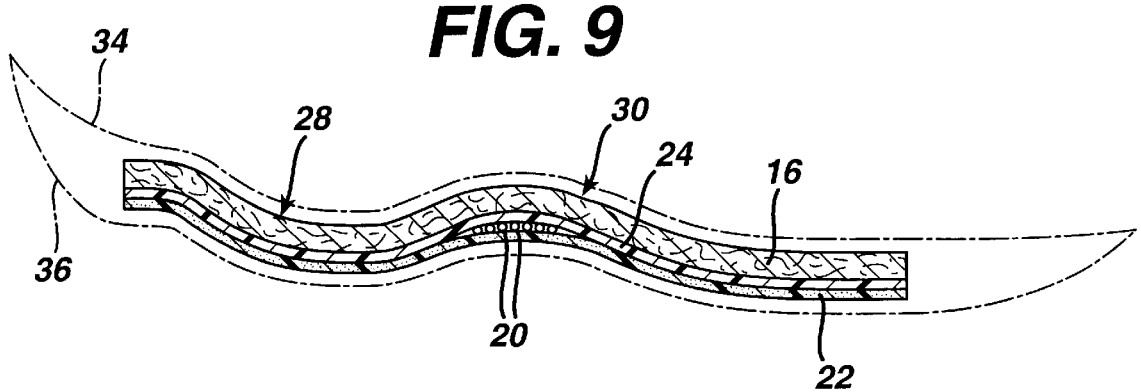
FIG. 9 is a longitudinal cross-sectional view along line IX—IX of the absorbent product of FIG. 3 during use.

A longitudinal cross-section along line IX—IX in FIG. 3 after use takes on the configuration illustrated in FIG. 9. The downward cup 28 in FIG. 9 coincides with the labia of the user, and the upward projection 30 coincides with the perineal raphe of the user 34. The ability of the absorbent product 10 to closely conform to the user's body surface contours can be expected to improve sanitary protection of women using this product.

The comfort of the product 10 may be enhanced by covering or protecting at least a portion of the conforming means 18 with one or more cushioning means 32. The cushioning means 32 may comprise foam, rubber, fibers, woven or nonwoven fabrics, and the like. Preferably, the cushioning means 32 is located at the ends of the conformable segments 20, in a region in which conformable segments 20 may be bent, e.g., at the outside of a curve where the segments 20 have a minimal radius of curvature (See e.g., FIG. 8).

While the present invention may incorporate pressure sensitive adhesive positioning means 22 secured to the garment-facing side 14 of the product 10, it is preferred that the positioning means 22 be non-adhesive. Preferably, the positioning means 22 is a high-friction surface, such as a fibrous surface, a polymeric foam surface, a rubber surface, a non-adhesive, tacky surface, surface projections, e.g., hooks, and the like. Additional high-friction surfaces are disclosed in Lachapell et al., U.S. Pat. No. 4,834,739, herein incorporated by reference. As used herein the specification and the claims, the term "high-friction" includes surfaces which provide sufficient friction to prevent substantial movement of the absorbent product within the undergarment during use. More preferably, the positioning means 22 is a polymeric foam or rubber surface.

The absorbent product may be manufactured in accordance with known manufacturing methods as modified below. In one method, segments of the conforming means can be applied to previously formed absorbent products or to a web from which absorbent products can be removed. In another method, a preformed conforming means having a plurality of conformable segments located on an adhesive tape can be applied to previously formed absorbent products or to a web from which absorbent products can be removed. In yet another method, preformed conforming means or conformable segments can be unwound from a roll and laminated between a barrier surface of the absorbent product and a high-friction component, such as a polymeric foam layer.

The absorbent product can be used by placing it within a user's undergarment 36. In embodiments having wings or tabs, they can be wrapped around the side of the crotch portion of the undergarment 36 to stabilize the products during use. After the product has been worn and soiled, it can be replaced with a fresh absorbent product.

The specification and drawings discussed above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent product for wearing in a crotch portion of an undergarment, having a length dimension which is greater than a width dimension, a center region and two spaced longitudinal end regions comprising: an absorbent structure having a center region and two spaced, longitudinal end regions disposed between a body-facing surface and a garment-facing surface; and conforming means comprising an association of from about 3 to 50 adjacent, conformable segments, spanning 10–90 percent of the length dimension of the absorbent product and from about 50 to less than about 100 percent of the width dimension of the absorbent product, with some of the conformable segments oriented in the length dimension, and at least some of the conformable segments oriented in the transverse to the length dimension of the absorbent product, the conforming means having a Thwing-Albert bending force of about 1 to 250 g and being arranged and configured to provide malleable support to the absorbent product.

2. The absorbent product of claim 1 wherein the garment-facing surface comprises a high-friction surface.

3. The absorbent product of claim 1 wherein the conformable segments are metal wire segments.

4. The absorbent product of claim 1 wherein the conforming means has a Thwing-Albert bending force of about 10 to 150 g.

5. An absorbent product having a length dimension which is greater than a width dimension, a center region and two spaced longitudinal end regions for wearing in a crotch portion of an undergarment, comprising: an absorbent structure having a center region and two spaced, longitudinal end regions disposed between a body-facing surface and a high friction garment-facing surface; conforming means comprising an association of from about 3 to 50, adjacent conformable segments, spanning 10–90 percent of the length dimension and from about 50 to less than about 100 percent of the width dimension of the absorbent product, the conforming means having a Thwing-Albert bending force of about 1 to 250 g and with at least some of the conformable segments being arranged and configured transverse to the length dimension of the absorbent product and at least some of the conformable segments oriented in the length dimension, to provide malleable support to the absorbent product and lateral extensions for wrapping around a portion of the undergarment; whereby the absorbent product is capable of acquiring and maintaining a form corresponding to a user's surface anatomy by action of forces normally exerted on the absorbent product during use.

6. The absorbent product of claim 5 wherein the conforming means comprises an association of about 7 to 30 conformable segments.

7. The absorbent product of claim 5 wherein the conformable segments are metal wires.

8. The absorbent product of claim 5 wherein the conforming means has a Thwing-Albert bending force of about 10 to 150 g.

\* \* \* \* \*